(12) United States Patent
Natarajan et al.

(10) Patent No.: US 7,344,679 B2
(45) Date of Patent: Mar. 18, 2008

(54) METHOD AND APPARATUS FOR POINT OF CARE OSMOLARITY TESTING

(75) Inventors: Govindarajan Natarajan, Poughkeepsie, NY (US); James N. Humenik, LaGrangeville, NY (US); Scott D. Partington, Raleigh, NC (US); Srinivasa S. N. Reddy, LaGrangeville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/163,327

(22) Filed: Oct. 14, 2005

(65) Prior Publication Data

US 2007/0086927 A1 Apr. 19, 2007

(51) Int. Cl.
*G01N 15/06* (2006.01)
*G01N 33/00* (2006.01)
*G01N 33/48* (2006.01)
*B32B 5/02* (2006.01)
*B32B 27/04* (2006.01)

(52) U.S. Cl. .................... 422/82.01; 422/50; 422/68.1; 422/82.02; 422/100; 436/43; 436/63

(58) Field of Classification Search .................. 422/50, 422/68.1, 100, 82.01, 82.02; 436/43, 63
See application file for complete search history.

(56) References Cited

U.S. PATENT DOCUMENTS

| 4,269,197 | A | 5/1981 | Gilbard |
| 4,996,993 | A | 3/1991 | York |
| 5,143,080 | A | 9/1992 | York |
| 6,454,924 | B2 * | 9/2002 | Jedrzejewski et al. ...... 204/601 |
| 7,017,394 | B2 * | 3/2006 | Sullivan .................... 73/64.47 |
| 2004/0036485 | A1 | 2/2004 | Sullivan |

* cited by examiner

*Primary Examiner*—Brian Sines
(74) *Attorney, Agent, or Firm*—Joseph Petrokaitis; Hoffman, Warnick & D'Alessandro LLC (57) ABSTRACT

An apparatus and a method are disclosed for providing point of care testing for osmolarity of a bodily fluid. An apparatus is disclosed as having a fluid pathway passing through it for receiving and testing a sample fluid. The invention permits osmolarity testing of a sample fluid wherein the sample fluid has a volume of less than approximately 30 nL, and implements a method and device to measure fluid osmolarity in a clinical setting quickly and accurately, while also reducing evaporation of the fluid.

6 Claims, 7 Drawing Sheets

METHOD AND APPARATUS FOR POINT OF CARE OSMOLARITY TESTING

BACKGROUND OF THE INVENTION

1. Technical Field

The present invention relates generally to the field of devices for measuring the osmolarity of a relatively small volume of fluid, and in particular to a method and an apparatus for measuring, in vivo, the osmolarity of human tears.

2. Related Art

Dry eye syndrome (DES), a condition that occurs due to loss of water from the tear film, is one of the most common complaints seen by optometrists. Studies have found that DES is common in about 15% of patients over the age of 50, with prevalence increasing with age. Dry eye in general is caused by any condition that increases tear film evaporation, or by any condition that decreases tear production. For some patients, evaporation is increased as a result of having larger eyes. Larger eyes cause greater evaporation due to the larger surface area and the loss of water. Tear production can also decrease from any condition that decreases corneal sensation. Long-term contact lens wear, LASIK eye surgery, trauma to the 5th nerve, and certain viral infections cause decrease in corneal sensation. The treatment of DES depends on the severity of the condition. Some patients find relief from DES through the use of various artificial tears available on the market. Additionally, some patients are prescribed Omega-3 containing supplements. There are cases where "punctual plugs" need to be inserted to stop drainage of tears.

Osmolarity is the measure of the concentration of osmotically active particles in a solution, which may be quantitatively expressed in osmoles of solute per liter of solution. It is known that when the tear film loses water, salt and protein concentrations increase relative to the amount of water. When the concentration of salt and protein increases relative to the amount of water, osmolarity increases. Therefore, in order to diagnose and treat DES patients, it is desirable for a treating physician to quantify the osmolarity of a sample tear fluid. Some current osmolarity measurement methods and devices available include: osmotic pressure measurement, freezing point measurement, and vapor pressure measurement.

In one approach, an osmometer is used to measure the osmotic pressure exerted by a solution across a semi-permeable membrane. In this approach, a solvent and solution are separated by the semi-permeable membrane, which allows only solvent molecules to pass through. The osmotic pressure of the solution can be determined by measuring the excess pressure that must be applied to the solution to prevent the solvent from passing into the solution.

In another approach, the osmolarity of a sample fluid (e.g., a tear) can be determined by an ex vivo technique called "freezing point depression." In this technique, solutes or ions in a solvent (i.e., water) cause a lowering of the fluid freezing point from what it would be without the ions. In the freezing point depression analysis, the freezing point of the ionized sample fluid is found by detecting the temperature at which a quantity of the sample (typically on the order of about several milliliters) first begins to freeze in a container (e.g., a tube). To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. Deviation of the sample freezing point from 0 degrees C. is proportional to the solute level in the sample fluid (i.e., osmolarity value).

Another ex vivo technique for osmolarity testing measures vapor pressure. In this method, a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature sensor is raised to the dew point of the sample. The reduction in dew point proportional to water is then converted into osmolarity. However, because of induced reflex tearing, osmolarity readings are not as accurate. Similarly, in vivo techniques, which attempt to measure osmolarity by placing electrodes directly under the eyelid of a patient, are likely to induce reflex tearing. As a result the above-described approaches are neither convenient nor accurate for an eye doctor operating in a clinical environment.

There is a need for a clinically feasible, nanoliter-scale osmolarity measurement device, with the capability for reduced evaporation, that does not suffer from the problems of the related art.

SUMMARY OF THE INVENTION

An apparatus and a method are disclosed for providing point of care testing for osmolarity of a bodily fluid. An apparatus is disclosed as having a fluid pathway passing through it for receiving and testing a sample fluid. The invention permits osmolarity testing of a sample fluid wherein the sample fluid has a volume of less than approximately 1 mL, with a preferred volume of less than 30 nL, and implements a method and device to measure fluid osmolarity in a clinical setting quickly and accurately, while also reducing evaporation of the fluid.

A first aspect of the invention is directed to a sample receiving chip comprising: a substrate having a fluid pathway passing through the substrate for receiving a sample fluid, the fluid pathway including a first port, at least one second port, and a recessed channel, the recessed channel enclosed in the substrate; and at least two electrodes positioned in the substrate to contact the sample fluid in the recessed channel to measure properties of the sample fluid.

A second aspect of the invention is directed to a device for osmolarity testing, comprising: a base member; a sample receiving chip fixed to the base member for receiving a sample fluid; and a conduit fixed to the base member for depositing the sample fluid on the sample receiving chip, the conduit including a first end and a second end.

A third aspect of the invention is directed to a method for determining osmolarity of a sample fluid, comprising the steps of: communicating a sample fluid through a conduit fixed to a base member directly to a sample receiving chip; and determining osmolarity of the sample fluid.

The foregoing and other features of the invention will be apparent from the following more particular description of the embodiments of the invention.

BRIEF DESCRIPTION OF THE DRAWINGS

The embodiments of this invention will be described in detail, with reference to the following figures, wherein the like designations denote like elements, and wherein.

DETAILED DESCRIPTION

Exemplary embodiments are described below for measuring the osmolarity of a sample fluid. The embodiments are configured to provide quick and accurate testing of a relatively small amount of fluid.

Referring to FIGS. 1-4, a sample receiving chip for testing osmolarity of a sample fluid according to one embodiment of the invention is shown. It can be appreciated, that even though three substrate layers are shown in the present embodiment, any number of substrate layers can be used. Furthermore, while sample receiving chip 2 is initially discussed in isolation, during operation sample receiving chip 2 may be coupled to a device, as will be described further below, including a base member; sample receiving chip 2 fixed to the base member for receiving a sample fluid; and a conduit fixed to the base member for depositing the sample fluid on sample receiving chip 2. Coupling receiving chip 2 to a device allows for more convenient and effective point-of-care testing.

Figure 1A:
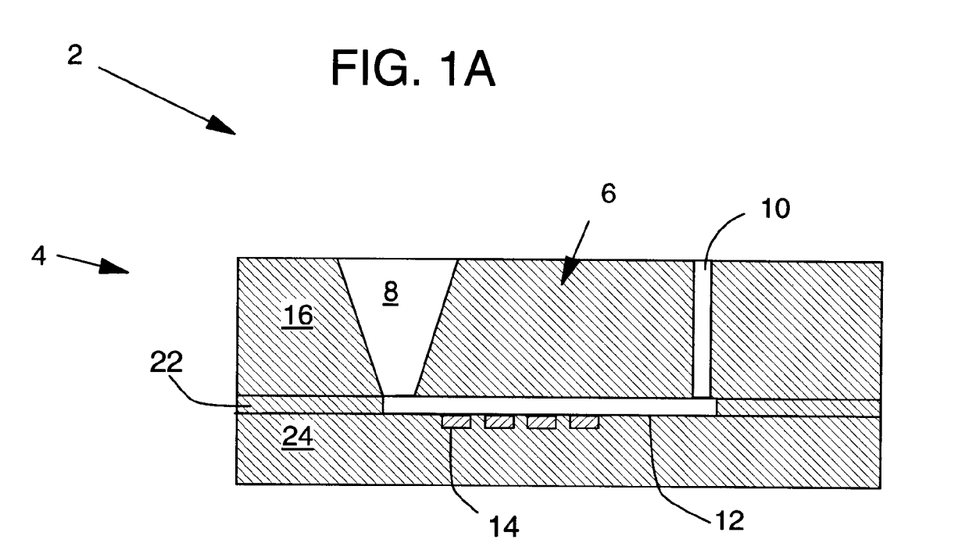
FIGS. 1A-B show a cross sectional view of a sample receiving chip according to one embodiment of the invention.
Figure 1B:
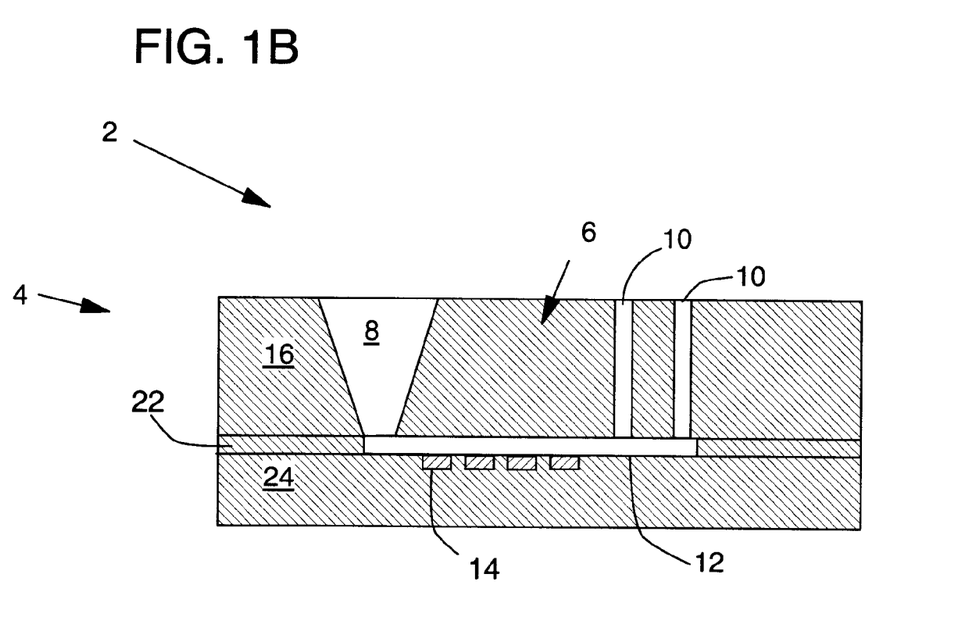

When the various substrate layers shown in FIGS. 1-4 are combined, sample receiving chip 2 comprises: substrate 4 having fluid pathway 6 passing through substrate 4 for receiving a sample fluid. Fluid pathway 6 may include a first port 8, at least one second port 10 (hereinafter simply "second port 10"), and a recessed channel 12. As shown in FIG. 1, recessed channel 12 is enclosed in substrate 4. Sample receiving chip 2 also includes at least two electrodes 14 positioned in substrate 4 to contact the sample fluid in the recessed channel to measure properties of the sample fluid. Electrode windows 18, which are shown in FIGS. 2A, 3, 5, 7, and 8, are not shown in FIG. 1 for clarity. However, it should be noted that substrate 4 may include electrode windows 8.

Figure 2A:
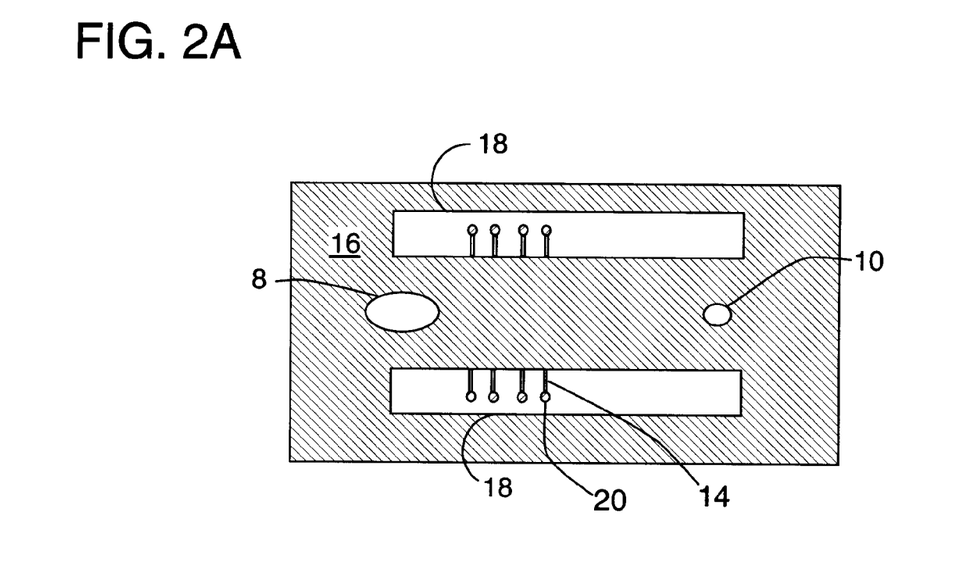
FIGS. 2A-B show a plan view of two embodiments of a first substrate layer of the sample receiving chip of FIG. 1.
Figure 2B:
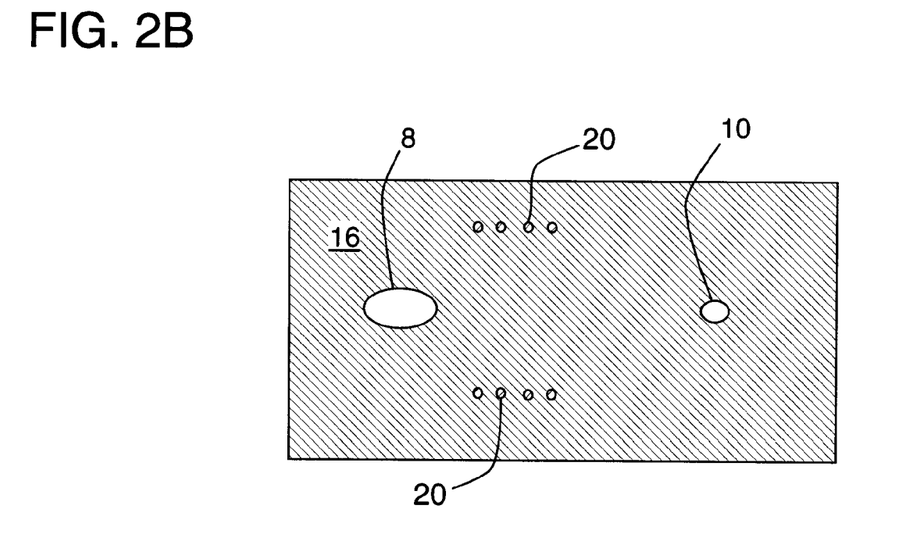

Referring to FIGS. 2A-B, a plan view of first substrate layer 16 is shown. First substrate layer 16 forms an upper layer of chip 2, as shown in FIG. 1. As shown in FIG. 2A, first port 8, second port 10, and electrode windows 18 are openings formed in first substrate layer 16 by, for example, mechanically punching-out portions of first substrate layer 16. It can be appreciated, however, that any technique for creating openings in a substrate layer can be used. As will be described in further detail below, at least two electrode windows 18 provide access to at least two electrodes 14. In an alternative embodiment, shown in FIG. 2B, first substrate layer 16 may include first port 8, and second port 10, but no electrode windows. As will be described in further detail below, when substrate 4 does not include electrode windows 18, substrate 4 includes at least two electrodes (not shown) connected to contacts 20 positioned on an external surface of substrate 4. Although contacts 20 are shown in FIG. 2B as circular in shape, it can be appreciated that contacts 20 can be any suitable geometric shape.

Figure 3:
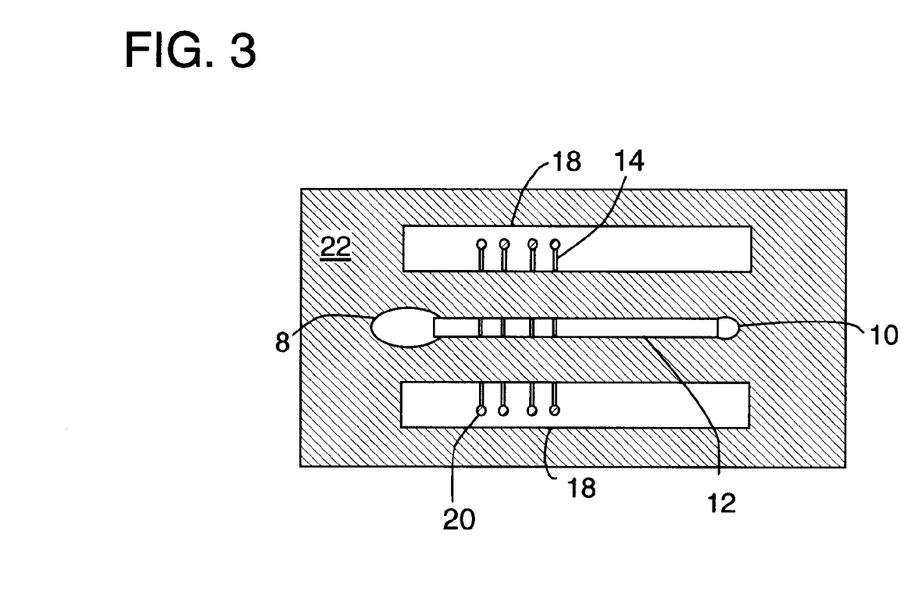
FIG. 3 shows a plan view of a second substrate layer of the sample receiving chip of FIG. 1.

Referring to FIG. 3, a plan view of second substrate layer 22 is shown. Second substrate layer 22 constitutes a middle layer of chip 2, as shown in FIG. 1. In this embodiment, second substrate layer 22 includes openings for first port 8, second port 10, and recessed channel 12. Additionally, second substrate layer 22 may include openings for electrode windows 18. First port 8, second port 10, and recessed channel 12 are formed, by example, by mechanically punching out the desired portion of second substrate layer 22. In a preferred embodiment, second substrate layer 22 is positioned below first substrate layer 16.

Figure 4:
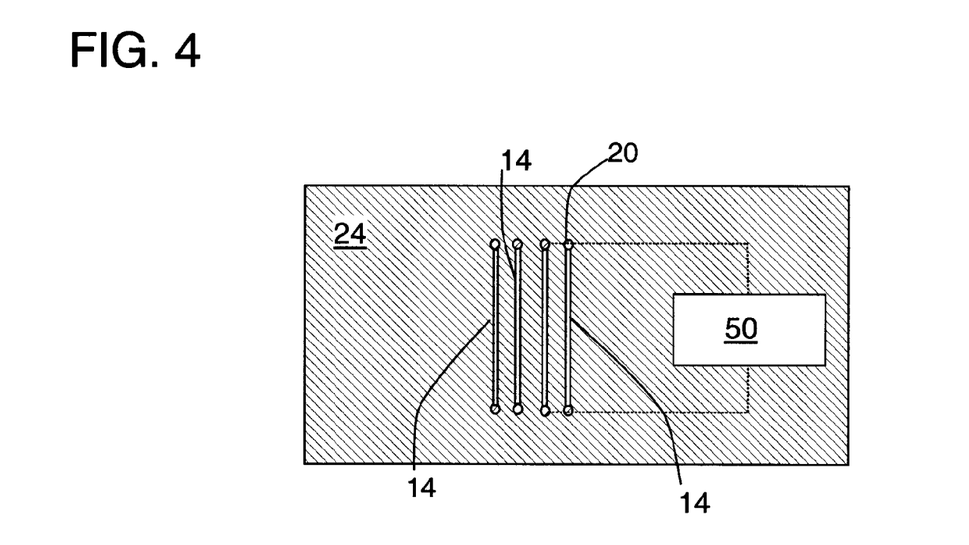
FIG. 4 shows a plan view of a third substrate layer of the sample receiving chip of FIG. 1.

FIG. 4 shows a plan view of third substrate layer 24. Third substrate layer 24 constitutes a bottom layer of chip 2, as shown in FIG. 1. Third substrate layer 24 comprises at least two electrodes 14 in the recessed channel to contact the sample fluid and contacts 20 to connect to testing circuit 50 to measure properties of the sample fluid. In a preferred embodiment, third substrate layer 24 is positioned below first substrate layer 16 and second substrate layer 22, respectively. Electrodes 14 are positioned under recessed channel 12 to make contact with the sample fluid, as shown in FIG. 3, and are preferably cosintered with multilayer ceramic.

Due to traditional manufacturing methods for ceramic substrates, traditional metal electrodes begin to deteriorate under the higher temperatures necessary to bond and cure the substrate. Ceramic particles and metal particles coalesce at different temperature ranges and rates during sintering. Therefore, reasonably matching metals and ceramics with similar densification rates helps to obtain controlled part dimensions (outer and feature dimensions), and defect free (cracks/breakage, etc) devices. In the present invention, a cordierite based glass ceramic is preferred as the base device material and a copper+nickel+glass ceramic is preferred as the conductor material. The nickel and copper combination helps to avoid corrosion during use and storage of the chip, as chemical reactions, such as corrosion, negatively interfere with measurement. Additionally, the maximum sinter temperature in a preferred embodiment is less than approximately 1000 degrees C.

Referring again to FIGS. 1-4, operation of a sample receiving chip 2 will now be described in greater detail. During operation, a relatively small amount of sample fluid is deposited into first port 8. In a preferred embodiment, reliable osmolarity measurement is obtained with a fluid sample volume of less than approximately 30 nL. The sample fluid passes through first port 8 and recessed channel 12 formed in substrate layers 16 and 22, respectively. First port 8 narrows as the sample liquid passes through first substrate layer 16, and second substrate layer 22. The fluid is drawn through first port 8 and recessed channel 12 by venting second port 10. It can be appreciated that first port 8 and second port 10 of sample receiving chip 2 may be a variety of geometric configurations, so long as first port 8 funnels the sample fluid into recessed channel 12 and second port 10 vents recessed channel 12. However, the geometries of first port 8, recessed channel 12, and second port 10, can influence fluid flow. Second port 10 can be designed to control the rate at which the sample fluid flows through recessed channel 12. As shown by FIG. 1B, additional second port 10 (or any number of additional second ports) can be added to further influence fluid flow through recessed channel 12. In a preferred embodiment, once the sample liquid is drawn through recessed channel 12 by capillary action, second port 10 becomes partially filled with the sample fluid, the sample fluid being held by surface tension. Furthermore, a hydrophilic substrate surface is preferably used to promote fluid flow through recessed channel 12. This combination of surface chemistry, channel geometry, and vent geometry is used to control flow uniformity, rate, and residence time.

Figure 5:
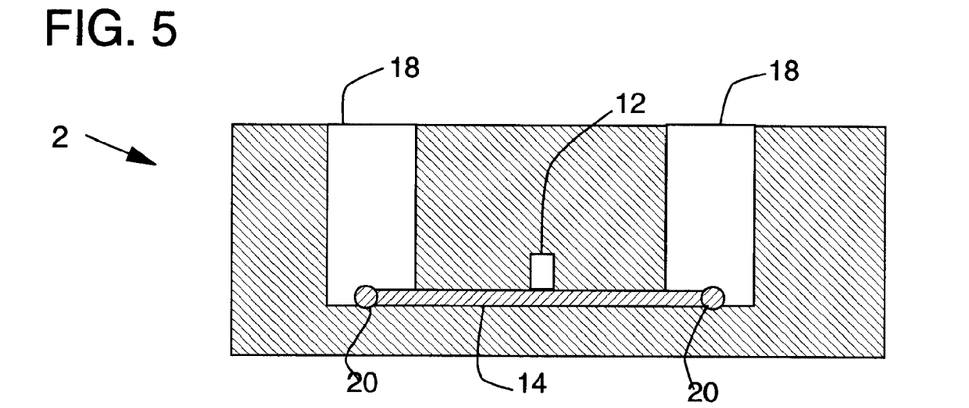
FIG. 5 shows a cross sectional view of the electrode windows which provide access to electrodes for osmolarity testing.
Figure 6A:
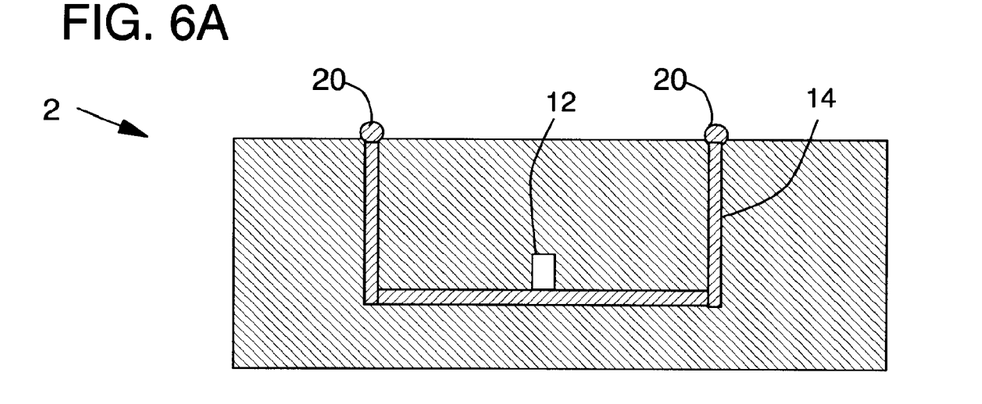
FIGS. 6A-B show a cross sectional view of the electrode contacts positioned on different surfaces the sample receiving chip of FIG. 1.
Figure 6B:
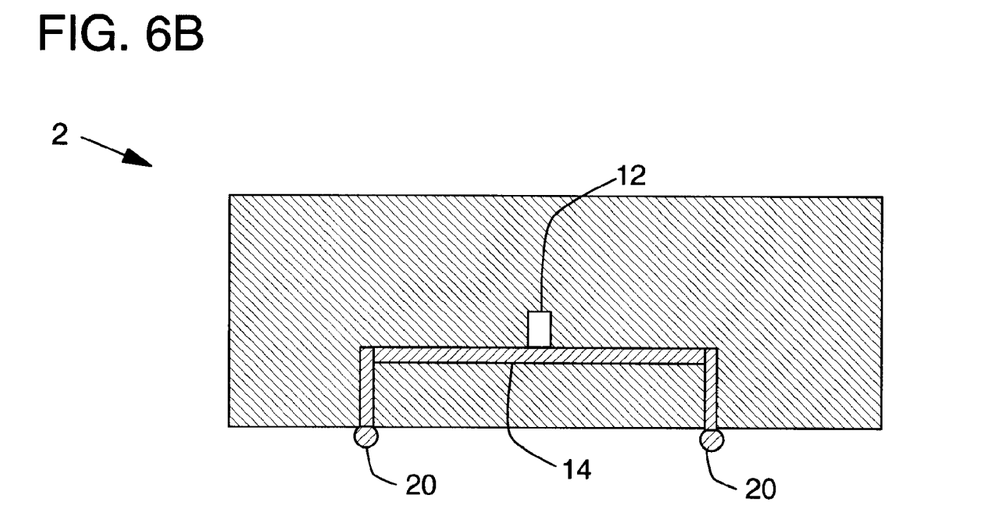

Referring now to FIG. 5, a cross sectional view of one embodiment of substrate 4, including electrode windows 18, is shown. In this embodiment, recessed channel 12, containing the sample fluid, flows in a direction perpendicular to electrodes 14. It can be appreciated however, that different electrode configurations can be used, as long as the sample fluid comes into contact with the electrodes. Also shown in FIG. 5, at least two electrode windows 18 provide access to at least two electrodes 14. An external measurement device (not shown) can be inserted into the openings formed by electrode windows 18 to contact electrodes 14, via contacts 20. As a result, the conductivity of the sample fluid may be determined. In alternative embodiments, as shown in FIGS. 6A-B, at least two electrodes 14 are connected to contacts 20 that extend to and are positioned on an external surface of substrate 4. As shown by comparing FIGS. 6A-B, contacts 20 may be positioned on various external surfaces of substrate 4, so long as electrodes 14 come into contact with the sample fluid flowing through recessed channel 12.

Figure 7:
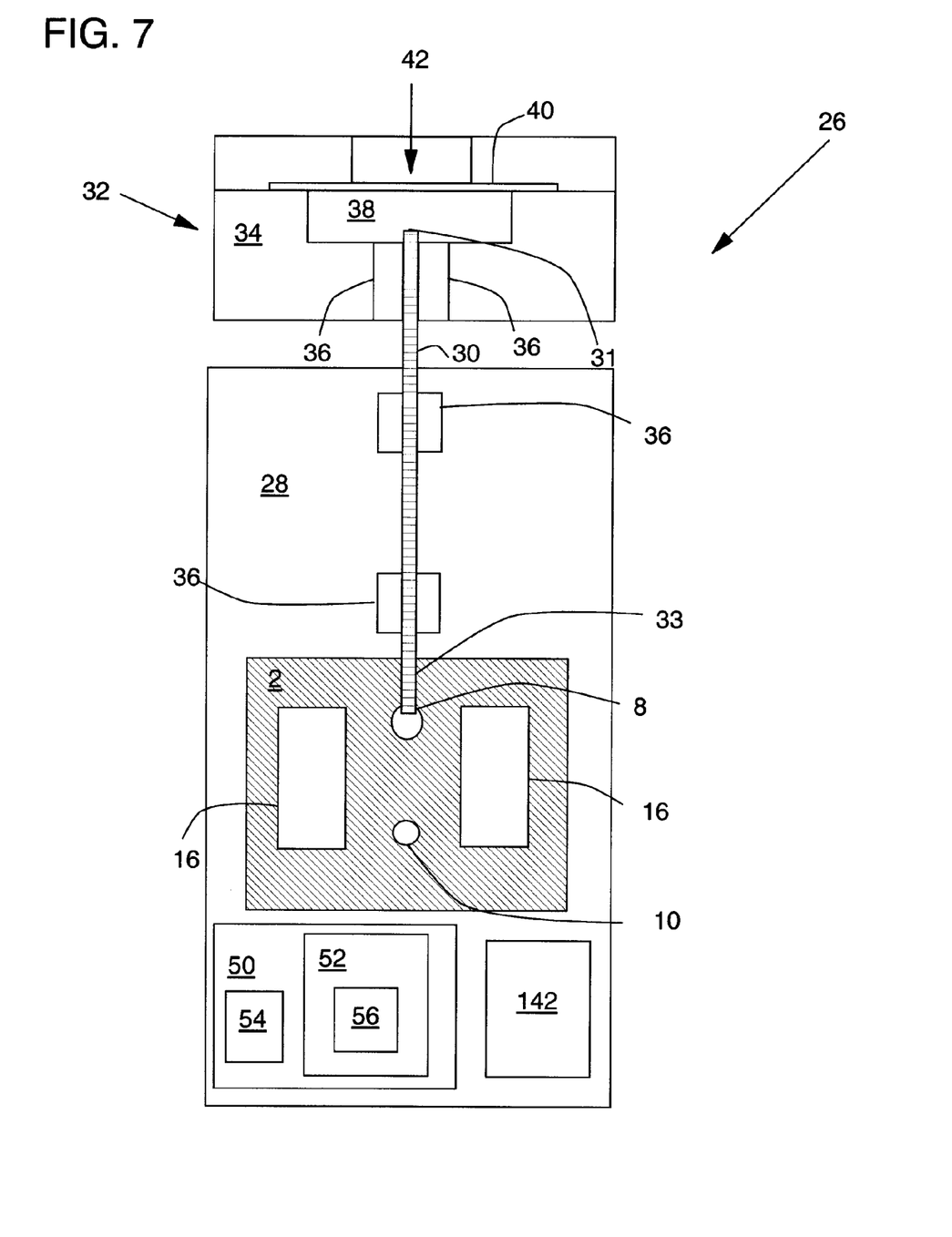
FIG. 7 shows a plan view an osmolarity testing device to collect a sample fluid and to test osmolarity of the sample fluid.

Referring now to FIG. 7, a point of care osmolarity testing device 26 is shown. In one embodiment, device 26 for testing osmolarity comprises: base member 28; sample receiving chip 2 fixed to base member 28 for receiving a sample fluid; and conduit 30 fixed to base member 28 for depositing the sample fluid on sample receiving chip 2. Conduit 30 includes first end 31 and second end 33. It should be noted, that sample receiving chip 2 may be substantially identical to that described above, except for any required mounting structure. In one embodiment, osmolarity testing device 26, as shown in FIG. 7, further includes capillary receptacle 32 including: base unit 34, including fastener 36 for fixing conduit 30 to base unit 34, and chamber 38 for receiving first end 31 of conduit 30. Conduit 30, containing the sample fluid, may be fastened to capillary receptacle 32. Chamber 38 includes substantially flexible partition 40. Device 26 also includes external pressure applying mechanism 42 to apply an external pressure to substantially flexible partition 40 for altering chamber pressure to discharge the sample fluid from second end 33 of conduit 30. Mechanism 42 may include structure, for example, to pump air, to provide a piezoelectric change that causes flexible partition 40 to expand and contract in a controlled manner, or any other now known or later developed structure to apply a force to substantially flexible partition 40.

Referring again to FIG. 7, a preferred method for determining osmolarity of a sample fluid will be described in greater detail. In one embodiment, a method for determining osmolarity of a sample fluid comprises the steps of: communicating a sample fluid through conduit 30 fixed to base member 28; and determining osmolarity of the sample fluid. Communicating a sample fluid through conduit 30 may include contacting an in vivo sample of bodily fluid on the human eye, whereby the sample fluid is drawn into conduit 30 by capillary force. Typically, a treating physician opens the lower eyelid of a patient and touches the tear in the tear cavity with conduit 30. The tear is drawn into conduit 30 by capillary force and held by surface tension. After the sample fluid is collected by conduit 30, conduit 30 is placed in capillary receptacle 32. The receptacle contains fastener 36 to isolate first end 31 of conduit 30 extending into chamber 38. In the present embodiment, the step of communicating also includes applying external pressure 42 to base unit 34, base unit 34 including chamber 38 for receiving first end 31 of conduit 30, wherein chamber 38 includes substantially flexible partition 40. A positive external pressure 42, such as low-pressure air, is applied to substantially flexible partition 40. Partition 40 transfers the pressure to chamber 38 and forces the sample fluid out as a drop from second end 33 of conduit 30.

Next, the osmolarity of the sample fluid is determined by a testing circuit 50. The osmolarity of the sample fluid can be measured by sensing the energy transfer properties of the sample fluid. The energy transfer properties can include, for example, electrical conductivity, such that the impedance of the sample fluid is measured, given a particular current that is transferred into the sample fluid. Testing circuit 50 applies a current source across the electrodes of sample receiving chip 2. Osmolarity of the sample fluid may be determined by measuring the conductivity of the sample fluid using conductivity measuring device 52 to obtain a conductivity value and converting the conductivity value to a corresponding osmolarity value using conversion system 54 (e.g., by a calibration knowledge base). In this case, testing circuit 50 includes an electrical conductivity measurement circuit 56 to determine osmolarity of the sample fluid. For example, measurement circuitry 56 may provide electrical energy in a specified waveform (such as from a function generator) to the at least two electrodes bridged by the sample fluid. Furthermore, as shown in FIG. 7, base member 28 may include a device for communicating results to a user, e.g., a display device 142 for displaying a visual representation of the osmolarity value. Alternatively, the osmolarity results can be communicated and displayed at a remote location in any known fashion.

Figure 8:
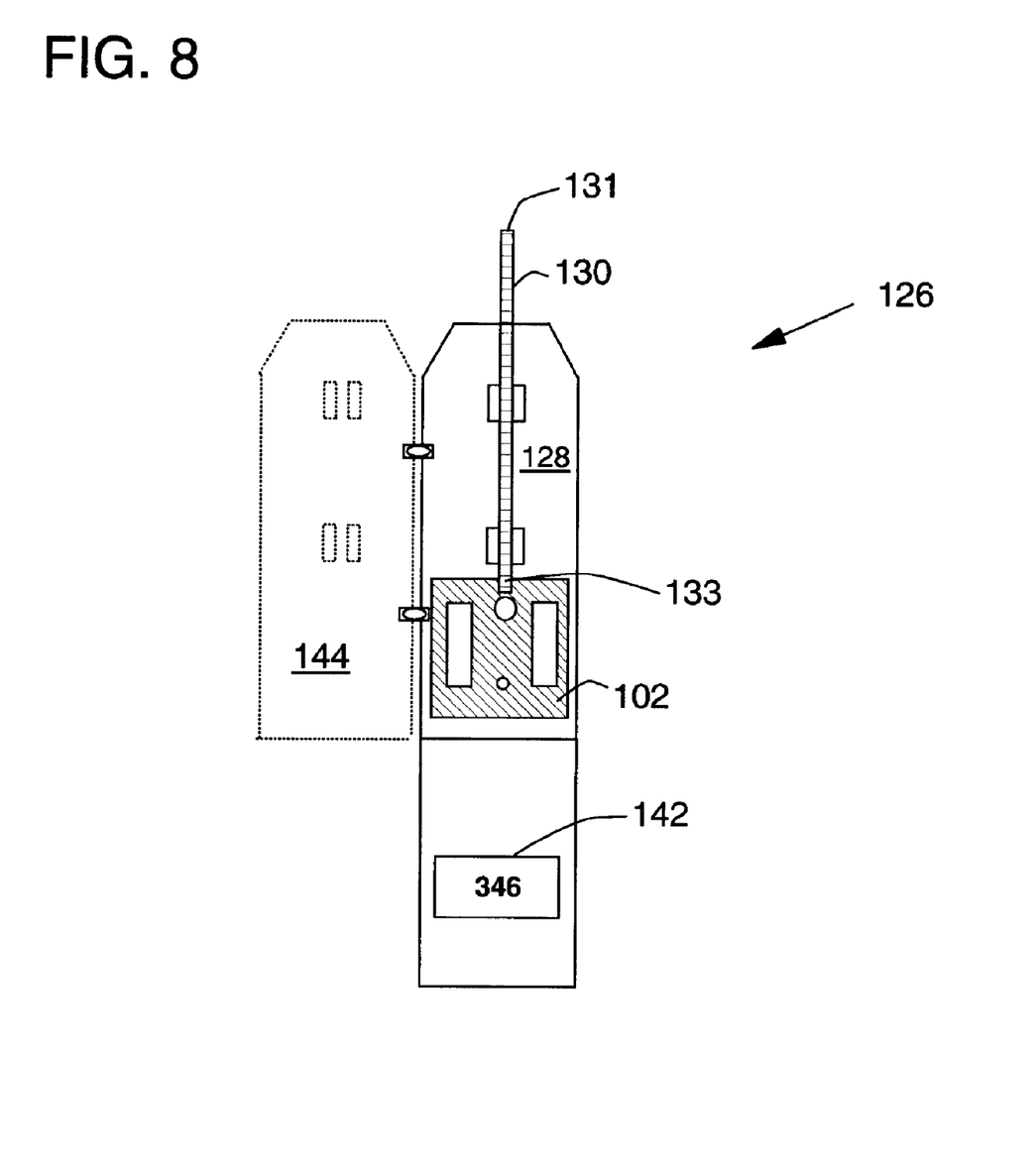
FIG. 8 shows a plan view of an osmolarity testing device to collect a sample fluid and to test osmolarity of the sample fluid.
Figure 9:
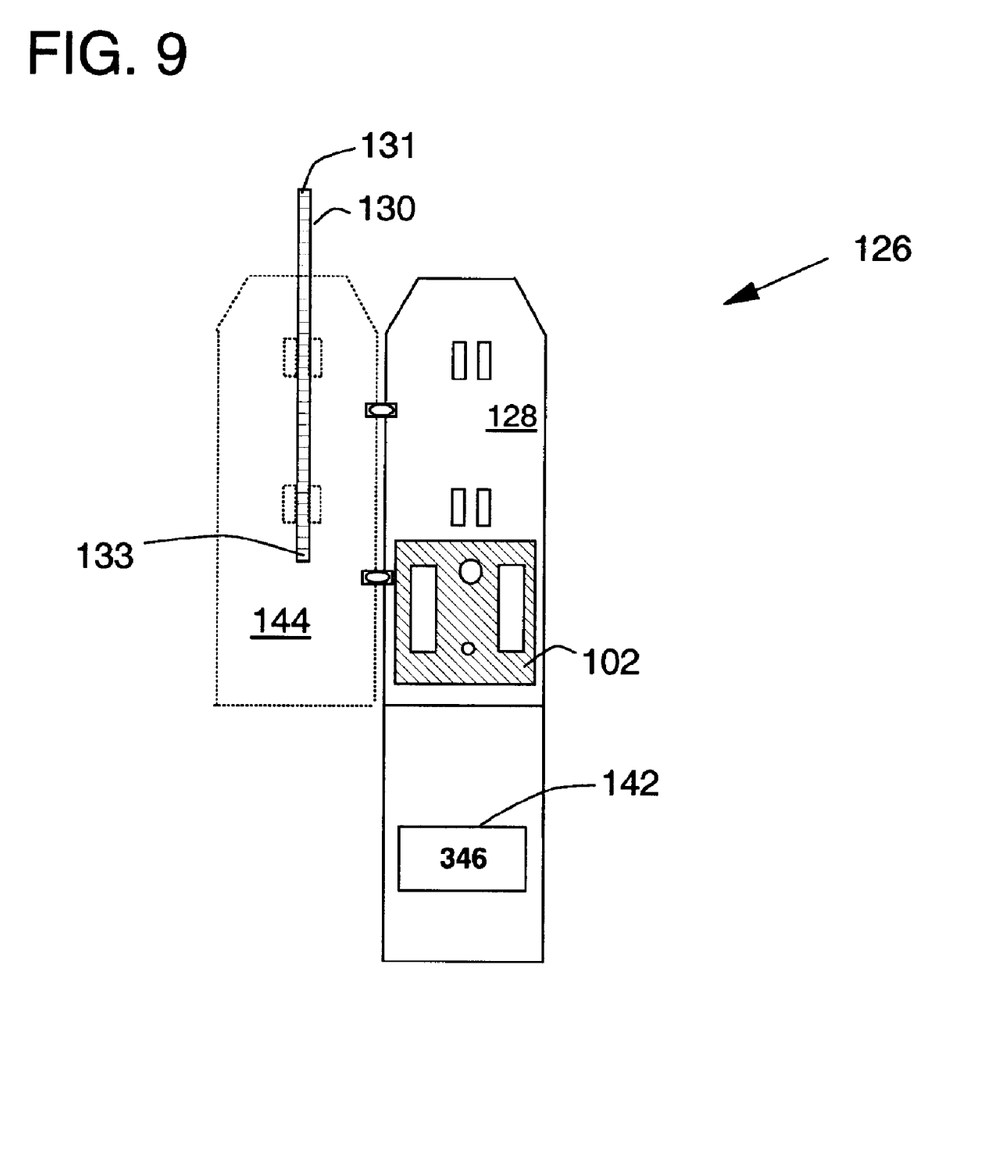
FIG. 9 shows a plan view of an osmolarity testing device to collect a sample fluid and to test osmolarity of the sample fluid.

In another embodiment, shown in FIG. 8, a treating physician may pre-position a conduit 130 to a base member 128 of an osmolarity testing device 126. Device 126 is similar to device 26 (FIG. 7) except Conduit 130 is fixed to base member 128 for depositing the sample fluid on sample receiving chip 102. A tear is then collected from the patient and is drawn into conduit 130 by capillary force. First end 131 of conduit 130 extracts the sample fluid, and second end 133 of conduit 130 deposits the sample fluid on sample receiving chip 102. Therefore, the method for determining osmolarity of a sample fluid, comprises: communicating a sample fluid through conduit 130 fixed to base member 128 directly to sample receiving chip 102; and determining osmolarity of the sample fluid. Furthermore, osmolarity testing device 133 may include hinged-cover 144 to protect conduit 130 and to make handling of device 126 more convenient. In another embodiment, as shown in FIG. 9, conduit 130 may be fastened to hinged-cover 44. It should be noted, that osmolarity testing device 126 can be a hand-held device, allowing for convenient and effective point-of-care treatment.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A device for osmolarity testing, comprising:
    a base member including an electrical conductivity measurement circuit configured to determine osmolarity of a sample fluid;
    a sample receiving chip fixed to the base member for receiving the sample fluid;
    a conduit fixed to the base member for depositing the sample fluid on the sample receiving chip, the conduit including a first end and a second end; and
    a capillary receptacle including:
        a base unit, including a fastener for fixing the conduit to the base unit, and a chamber for receiving the first end of the conduit, the chamber including a substantially flexible partition; and
        a mechanism for applying external pressure to the substantially flexible partition for altering chamber pressure to discharge the sample fluid from the second end of the conduit.

2. A device for osmolarity testing, comprising:
    a base member including an electrical conductivity measurement circuit configured to determine osmolarity of a sample fluid;
    a sample receiving chip fixed to the base member for receiving the sample fluid; and a conduit fixed to the base member for depositing the sample fluid on the sample receiving chip, the conduit including a first end and a second end; wherein the sample receiving chip comprises:
        a substrate having a fluid pathway passing through the substrate for receiving a sample fluid, the fluid pathway including a first port, at least one second port, and a recessed channel, the recessed channel enclosed in the substrate; and
        at least two electrodes positioned in the substrate to contact the sample fluid in the recessed channel to measure properties of the sample fluid.

3. The device of claim 2, wherein the substrate further comprises one of:
    a) at least two electrode windows to provide access to the at least two electrodes; and
    b) the at least two electrodes connected to contacts, the contacts positioned on an external surface of the substrate.

4. The device of claim 2, wherein the substrate is cordierite-based glass ceramic and the at least two electrodes are cosintered with copper, nickel, and glass ceramic.

5. The chip of claim 2, wherein the first port funnels the sample fluid into the recessed chamber and the at least one second port vents the recessed channel.

6. The device of claim 2, wherein the first end of the conduit extracts the sample fluid and the second end of the conduit deposits the sample fluid on the sample receiving chip.

* * * * *